(12) United States Patent
Wu et al.

(10) Patent No.: US 6,274,177 B1
(45) Date of Patent: Aug. 14, 2001

(54) **METHOD OF PREPARING AN EXTRACT POTENT IN ANTI-INFLAMMATION AND ANTI-PLATELET AGGREGATION FROM *ZINGIBER OFFICINALE* AND PHARMACEUTICAL COMPOSITIONS CONTAINING SAID EXTRACT**

(75) Inventors: Tian-Shung Wu, Tainan; Sheng-Chu Kuo, Taichung; Che-Ming Teng; Feng-Nien Ko, both of Taipei, all of (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/648,662

(22) Filed: Aug. 26, 2000

(51) Int. Cl.⁷ .................................................. A61K 35/78
(52) U.S. Cl. ............................. 424/756; 424/773
(58) Field of Search ................. 424/195.1, 773, 424/756

(56) References Cited

U.S. PATENT DOCUMENTS

| | | | |
|---|---|---|---|
| 5,494,668 | * 2/1996 | Patwardhan | 424/195.1 |
| 5,683,698 | * 11/1997 | Chavali et al. | 424/195.1 |
| 5,716,928 | * 2/1998 | Benet et al. | 514/11 |
| 5,804,603 | * 9/1998 | Chen | 513/630 |
| 5,908,628 | * 6/1999 | Hou | 424/195.1 |

OTHER PUBLICATIONS

BRS Computer Abstract JPAB JP407258104A Suzuki "Cancer Metastasis Suppressing Agent", Oct. 1995.*
BRS Computer Abstract JPAB JP07205777 Sugimoto et al "Synthesis Promoter for Neurotrophy Factor", Jan. 1995.*
BRS Computer Abstract JPAB JP406107556 Iwasaki et al "Chinese Analgesic Composed Exclusively of Herb Drug", Oct. 1995.*

* cited by examiner

*Primary Examiner*—Herbert J. Lilling
(74) *Attorney, Agent, or Firm*—Jackson Walker L.L.P.

(57) ABSTRACT

A method of preparing an extract from *Zingiber officinale*, which is potent in anti-inflammation and anti-platelet aggregation, includes the following steps: a) preparing a crude liquid from rhizomes of ginger by extraction with an organic solvent or by distillation with steam; b) introducing the crude liquid to a reverse phase chromatography column, and eluting the column with water, a first eluent and a second eluent having a polarity weaker than that of the first eluent but stronger than that of chloroform, so that a first eluate resulting from elution of the first eluent and a second eluate resulting from elution of the second eluent are obtained; c) removing the first eluent from the first eluate by evaporation, so that a first concentrated eluate is obtained and is able to used as the potent extract; and d) removing the second eluent from the second eluate by evaporation, so that a second concentrated eluate is obtained and is able to used as the potent extract.

37 Claims, No Drawings

METHOD OF PREPARING AN EXTRACT POTENT IN ANTI-INFLAMMATION AND ANTI-PLATELET AGGREGATION FROM *ZINGIBER OFFICINALE* AND PHARMACEUTICAL COMPOSITIONS CONTAINING SAID EXTRACT

FIELD OF THE INVENTION

The present invention is related to a method of preparing an extract potent in anti-inflammation and anti-platelet aggregation from *Zingiber officinale*.

BACKGROUND OF THE INVENTION

Chinese crude drugs or spices eg. *Zingiber officinale, Eugenia caryophyllata, Allium sativum*, have been used in medicine and in flavoring foods. Crude ginger is used as an anti-emetic and expectorant, an anti-tussive and accelerator of the digestive organs. Semi-dried old crude ginger is also used for stomachache, chest pain, low back pain, cough, common cold and as a cure for a form of edema being called "stagnate of water". Zingerone is the major component which accounts for the spicy character of ginger; gingerol and shogaol are other pungent components in ginger. Gingerol has cardio-tonic action, suppresses the contraction of isolated portal veins in mice, and modulates the eicosanoid-induced contraction of mouse and rat blood vessels. Shogaol exhibits pressor response. Both gingerol and shogaol are mutagenic, whereas zinger and zingerone have been found to exhibit antimutagenic activity. Shogaol has inhibitory activity on the carrageenin-induced paw edema and platelet aggregation [U.S. Pat. No. 5,804,603, Background of the Invention].

Heretofore, many reports have shown that *Zingiber officinale* exhibits various physiological activities. Typical examples include a cancer metastasis suppressing agent disclosed in Japan patent publication No. 7-258104; a synthesis promoter for neurotropic factor, which is effective for nerve deteriorative diseases such as Alzheimer's dementia or Parkinson's disease, disclosed in Japan patent publication No. 7-25777; an anti-rheumatic agent disclosed in Japan patent publication No. 6-293653, U.S. Pat. Nos. 5,494,668 and 5,683,698; an antimicrobial composition disclosed in Japan patent publication No. 6-227931; and an analgesic composition disclosed in Japan patent publication No. 6-107556. Ginger contains 1–4% essential oil (oleoresin). During the last 45 years many chemical investigations have been carried out on the constituents of the essential oil. Altogether more than 200 different volatiles have been identified in essential oil wherein the pharmacological activity is confined. The essential oil contains a mixture of various terpenes as well as some other non-terpenoid compounds. Although this is mostly speculative, the experimental data and observations suggest that ginger inhibits both the cyclooxygenase and lypoxygenase products, i.e. it can be a dual inhibitor of eicosanoid synthesis. In all 56 patients (28 with rheumatoid arthritis, 18 with osteoarthritis and 10 with muscular discomfort) used powdered ginger against their afflictions. Amongst the arthritis patients more than three-quarters experienced, to varying degrees, relief in pain and swelling. All the patients with muscular discomfort experienced relief in pain. None of the patients reported adverse effects during the period of ginger consumption which ranged from 3 months to 2.5 years. (Srivastava and Mustafa; Medical Hypotheses; 1992; 39 342–348).

Non-steroidal anti-inflammatory drugs have three major actions, all of which are related to inhibition of cyclo-oxygenase resulting in decreased formation of prostanoids. Firstly, an anti-inflammatory action achieved by reduced production of vasodilator prostaglandins (PGE2, PGI2) which means less vasodilation and, indirectly less edema. Secondly, an analgesic effect achieved by reduced prostaglandin production (less sensitization of nociceptive nerve endings to the inflammatory mediators bradykinin and 5-hydroxytryptamine). Thirdly, an antipyretic effect which is probably due to a decrease in the mediator PGE2 generated in response to inflammatory pyrogens, much as interleukin-1. Since ginger inhibits prostanoid synthesis and also products of 5-lipoxygenase, its ameliorative effects in arthritis and muscular discomforts could be related to reduced formation of prostanoids and leukotrienes. Because of such a possibility a decrease in the carageenan-induced edema formation in the rat's paw after 3 g of ginger extract administration has been demonstrated and the potency of the extract in the acute inflammation test appears to be comparable to that exhibited by acetyl salicylic acid reported in the same study. (Mascolo N. et al Journal of Ethnopharmocology 1989, 27, 129–140).

SUMMARY OF THE INVENTION

The present invention provides extracts from rhizomes of ginger which show an activity in an in vitro anti-platelet aggregation test and an inhibitory activity on the carrageenin-induced paw edema. The extracts are prepared by extracting rhizomes of ginger with an organic solvent (such as ethyl ether, acetone, methanol and ethanol) or supercritical $CO_2$, or by steam distilling rhizomes of ginger to obtain a crude liquid, and subjecting said crude liquid to a reverse phase chromatography to obtain the extracts containing shogaols, gingerols and/or dehydrogingerdione.

DETAILED DESCRIPTION OF THE INVENTION

As introduced in the Background of the Invention, ginger has been used for anti-inflammation and pain relief.

The present invention is to provide an effective method of preparing a product potent in anti-inflammation and in anti-platelet aggregation from rhizomes of ginger. The potent product prepared in accordance with the method of the present invention has a substantially constant composition, so that the pharmaceutical effects thereof are definite.

The effective method of preparing product potent in anti-inflammation and in anti-platelet aggregation from rhizomes of ginger according to the present invention comprises the following steps:

a) preparing a crude liquid from rhizomes of ginger;

b) introducing the crude liquid to a reverse phase chromatography column, and eluting the column with water, a first eluent and a second eluent in sequence, said second eluent having a polarity weaker than that of the first eluent but stronger than that of chloroform, so that a first eluate resulting from elution of the first eluent and a second eluate resulting from elution of the second eluent are obtained;

c) removing the first eluent from the first eluate by evaporation, so that a first concentrated eluate is obtained and is able to be used as the potent product; and d) removing the second eluent from the second eluate by evaporation, so that a second concentrated eluate is obtained and is able to be used as the potent product;

wherein step a) comprises steps i) to iv), or comprises step I), step I'), or step I"), wherein said steps i) to iv) are:

i) shedding fresh rhizomes of ginger and filtering the resulting mixture to obtain a filtrate and a residue;

ii) extracting the filtrate with a first organic solvent, recovering the resulting extraction solution of the first organic solvent, and evaporating the first organic solvent from the extraction solution to obtain a first concentrated extraction solution;

iii) extracting the residue with a second organic solvent, recovering the resulting extraction solution of the second organic solvent, and evaporating the second organic solvent from the extraction solution to obtain a second concentrated extraction solution; and iv) combining the first concentrated extraction solution and the second concentrated extraction solution to obtain the crude liquid;

said step I) is:

I) extracting powder of dried rhizomes of ginger with the second organic solvent, recovering the resulting extraction solution of the second organic solvent, and evaporating the second organic solvent from the extraction solution to obtain the crude liquid;

said step I') is:

I') steam distilling powder of dried rhizomes of ginger, and concentrating the resulting distillate by evaporation to obtain the crude liquid; and said step I") is:

I") extracting powder of dried rhizomes of ginger with supercritical $CO_2$, recovering the resulting extraction solution of the supercritical $CO_2$, and evaporating $CO_2$ from the extraction solution to obtain the crude liquid.

The product potent in anti-inflammation and in anti-platelet aggregation prepared according to the method of the present invention preferably comprises 0–10 mg 6-shogaol per gram of the product, 1–150 mg 6-gingerol per gram of the product, and 0–40 mg 6-dehydrogingerdione per gram of the product.

The present invention also provides an anti-inflammation pharmaceutical composition comprising a therapeutically effective amount of said crude liquid prepared in step a) of the method of the present invention, as an active ingredient, in admixture with a pharmaceutically acceptable carrier or diluent for the active ingredient.

The present invention also provides a pharmaceutical composition for the inhibition of aggregation of platelets, which comprises a therapeutically effective amount of said crude liquid prepared in step a) of the method of the present invention, as an active ingredient, in admixture with a pharmaceutically acceptable carrier or diluent for the active ingredient.

The present invention also provides an anti-inflammation pharmaceutical composition comprising a therapeutically effective amount of said product prepared according to the method of the present invention, as an active ingredient, in admixture with a pharmaceutically acceptable carrier or diluent for the active ingredient. Preferably, said product prepared according to the method of the present invention is the first concentrated eluate prepared in step c). Alternatively, said product prepared according to the method of the present invention is the second concentrated eluate prepared in step d).

The present invention also provides a pharmaceutical composition for the inhibition of aggregation of platelets, which comprises a therapeutically effective amount of said product prepared according to the method of the present invention, as an active ingredient, in admixture with a pharmaceutically acceptable carrier or diluent for the active ingredient. Preferably, said product prepared according to the method of the present invention is the first concentrated eluate prepared in step c). Alternatively, said product prepared according to the method of the present invention is the second concentrated eluate prepared in step d).

Preferably, said first eluent is methanol, and said second eluent is acetone.

Preferably, step a) of the method of the present invention comprises steps i) to iv).

Preferably, said first organic solvent is ethyl ether.

Preferably, said second organic solvent is acetone, methanol, ethanol or a combination thereof. More preferably, said second organic solvent is acetone.

Preferably, step a) of the method of the present invention comprises step I).

Preferably, step a) of the method of the present invention comprises step I').

Preferably, step a) of the method of the present invention comprises step I").

A suitable reverse phase chromatography column for use in the method of the present invention includes (but is not limited thereto) a reverse phase chromatography column packed with a porous resin, for examples Diaion HP-20 (Mitsubishi Co.), Sephadex LH-20 (Pharmicia Co.) and RP-18 (Nacalai tesque Co.).

Without further elaboration, it is believed that the above description has adequately enabled the present invention. The following specific examples are, therefore, to be construed as merely illustrative, and not limitations on the remainder of the disclosure in any way whatsoever.

DETERMINATION OF ACTIVE INGREDIENTS

In the following examples, high performance liquid chromatography (abbreviated as HPLC) was used to determine the active ingredients of the products prepared therein. HPLC spectra were recorded on a HPLC instrument (HPLC Shimadzu LC-10AT, Japan) using a Cosmosil 5C-18 column (250 mm×4.6 mm, packed with particles having 5 $\mu$m diameter) by an elution method. An HPLC sample was prepared by diluting an appropriate amount of a product with a mobile phase solution (hydrogen cyanide:water= 65:35, V/V) to 25 ml, and filtered with a 0.25 $\mu$m membrane. The filtrate was introduced into the HPLC column, and eluted with the mobile phase solution. An UV detector (Shimadzu SPD-6AV, Japan) was used to detect the absorption of the eluate at 230 nm.

EXAMPLE 1

2100 g of fresh rhizomes of ginger were shredded and filtered to obtain a filtrate and a residue. 500 ml of the filtrate was extracted with 500 ml ethyl ether three times, the organic phase layers were separated from the aqueous phase layers, and combined. Ethyl ether was evaporated from the combined extraction solution in vacuo to obtain a concentrated ethyl ether extraction product (I-OE). The ginger residue was extract with 3000 ml acetone three times, the extraction solutions were recovered by filtration, and combined. Acetone was evaporated from the combined extraction solution in vacuo to obtain a concentrated acetone extraction product (I-O) (14.5 g). To a reverse phase chromatography column 300 mm×30 mm packed with 180 g Diaion HP-20 resin having a diameter of 500 $\mu$–800 $\mu$ 7 g of a mixture of the concentrate ethyl ether extraction product (I-OE) and the concentrated acetone extraction product (I-O)

was injected. 1500 ml water, 2500 ml methanol, 2000 ml acetone and 2000 ml chloroform were used to carry out elution. The water eluate, methanol eluate, acetone eluate and chloroform eluate were collected separately, and concentrated in vacuo to obtain 0.27 g concentrated water eluate (I-OW), 1.45 g concentrated methanol eluate (I-OM), 2.68 g concentrated acetone eluate (I-OA), and 0.83 g concentrated chloroform eluate (I-OC). The amounts (mg) of 6-shogaol, 6-gingerol and 6-dehydrogingerdione per gram of the I-O, I-OM and I-OA determined by HPLC are listed in Table 1.

TABLE 1

| Content (mg/g) | I-O | I-OM | I-OA |
| --- | --- | --- | --- |
| 6-shogaol | 1.10 ± 0.14 | 1.15 ± 0.0 | — |
| 6-gingerol | 59.98 ± 0.99 | 103.37 ± 8.57 | 2.51 ± 0.89 |
| 6-dehydrogingerdione | 7.68 ± 0.42 | 8.94 ± 0.41 | — |

EXAMPLE 2

500 g of shade dried rhizomes of ginger were pulverized and the resulting powder was extracted with 30 L acetone trice (each time with 10 L). The three extraction solutions were combined together after filtration, and then concentrated in vacuo to obtain 24 g of concentrated acetone extraction product (II-O). To a reverse phase chromatography column packed with 600 g Diaion HP-20 resin 20 g of the concentrated acetone extraction product (II-O) was injected, which was then eluted with 4 L water, 6.5 L methanol, 15 L acetone and 5 L chloroform in sequence. The water eluate, methanol eluate, acetone eluate and chloroform eluate were collected separately, and concentrated in vacuo to obtain 2.5 g concentrated water eluate (II-OW), 7.1 g concentrated methanol eluate (II-OM), 6.9 g concentrated acetone eluate (II-OA), and 3.5 g concentrated chloroform eluate (II-OC). The amounts (mg) of 6-shogaol, 6-gingerol and 6-dehydrogingerdione per gram of the II-O, II-OM and II-OA determined by HPLC are listed in Table 2.

TABLE 2

| Content (mg/g) | II-O | II-OM | II-OA |
| --- | --- | --- | --- |
| 6-shogaol | 1.98 ± 0.00 | 4.96 ± 0.00 | — |
| 6-gingerol | 43.06 ± 0.84 | 70.87 ± 1.85 | 2.54 ± 0.00 |
| 6-dehydrogingerdione | 9.33 ± 0.85 | 19.15 ± 4.57 | 2.35 ± 0.28 |

EXAMPLE 3

10 Kg of shade dried rhizomes of ginger were pulverized and the resulting powder was steam distilled for five hours. The distillate was concentrated in vacuo to obtain 410 g of concentrated distillate (III-O). To a reverse phase chromatography column packed with 600 g Diaion HP-20 resin 20 g of the concentrated distillate (III-O) was injected, which was then eluted with 4.5 L water, 4.5 L methanol, 3 L acetone and 5 L chloroform in sequence. The water eluate, methanol eluate, acetone eluate and chloroform eluate were collected separately, and concentrated in vacuo to obtain 0.03 g concentrated water eluate (III-OW), 14.5 g concentrated methanol eluate (III-OM), 0.85 g concentrated acetone eluate (III-OA), and 0.2 g concentrated chloroform eluate (III-OC). The concentrated distillate (III-O) contains no 6-shogaol, 6-gingerol and 6-dehydrogingerdione determined by HPLC.

EXAMPLE 4

10 g of powder of shade dried rhizomes of ginger was extracted with 1000 ml acetone at 50° C. for two hours. The extraction solution was separated and concentrated in vacuo (40° C., 75 mmHg) to obtain a concentrated acetone extraction product (IV-O). The color and viscosity of the product (IV-O) together with its yield are listed in Table 3.

EXAMPLE 5

10 g of powder of shade dried rhizomes of ginger was steam distilled, and the oily distillate after being separated from the aqueous distillate was freeze dried to obtain an oily extract (V-O). The color and viscosity of the oily extract (V-O) together with its yield are listed in Table 3.

EXAMPLE 6

To 10 g of powder of shade dried rhizomes of ginger in a 250 ml extraction chamber $CO_2$ was introduced at a flow rate of 45 L/min, wherein the chamber pressure was controlled at 2500 to 4000 psia with a high pressure pump (Model No. EK-1, LEWA Co., US) and the chamber temperature was maintained at 35–60° C. with a heat exchanger (Model No. H-2410, HOTEC Co., US) and an exterior circulation system. The extraction was stopped when the volume of $CO_2$ introduced reached 300 L, and a supercritical $CO_2$ extraction product (VI-O) was obtained after evaporation of $CO_2$. The color and viscosity of the product (VI-O) together with its yield are listed in Table 3. The contents of pungent components determined by HPLC are listed in Table 4.

TABLE 3

|  | IV-O | V-O | VI-O |
| --- | --- | --- | --- |
| L* | 87.6 | 80.4 | 96.3 |
| A* | −9.1 | −0.1 | −9.6 |
| B* | 31.1 | 9.6 | 22.0 |
| Viscosity (cPs) | 15.6 | 11.8 | 12.1 |
| Yield (%) | 3.8 | 2.2 | 3.9 |

*the values of L, A, and B were determined by using a Σ90 color measuring system, (Nippon Denshoku Inc, Co., Ltd., Japan), wherein L represents lightness, A is the red/green difference and B is the yellow/blue difference.

TABLE 4

| Content (mg/g) | VI-O |
| --- | --- |
| 6-shogaol | 17.30 ± 0.00 |
| 6-gingerol | 26.29 ± 0.00 |
| 6-dehydrogingerdione | 19.20 ± 1.19 |

EXAMPLE 7

Antiplatelet Assay

Blood, collected from the marginal ear vein of rabbits was mixed with EDTA (100 mM) in a volume ratio of 14:1 and centrifuged at 90 g for 10 min at room temperature to obtain platelet-rich plasma. The latter was further centrifuged at 500 g for 10 min, the upper plasma-rich layer was removed therefrom, and the remaining bottom layer was suspended with Tyrode's solution containing 2 mM EDTA but no calcium. The suspension was further centrifuged at 500 g for 10 min and the platelets were suspended with Tyrode's solution without EDTA. After centrifugation at the same conditions, the platelets were suspended with Tyrode's solution having the following compositions (mM): NaCl (136.8), KCl (2.8), $NaNCO_3$ (11.9), $MgCl_2$ (1.1), $NaH_2PO_4$ (0.33), $CaCl_2$ (1.0), glucose (11.2) and borine serum albumin (0.35%). Platelet numbers were determined with a Coulter Counter (Model ZM) and adjusted to $4.5 \times 10^8$ platelets/ml.

TABLE 5

The inhibitory effects of ginger extracts on platelet aggregation induced by arachidonic acid and collagen[a]

| Ginger extracts | Concentration for 50% inhibitory effect ($\mu$g/ml) | |
|---|---|---|
| | Arachidonic acid | Collagen |
| I-O | 3.8 ± 0.8 | 5.5 ± 0.4 |
| I-OM | 1.7 ± 0.3 | 2.7 ± 0.4 |
| II-O | 3.1 ± 0.5 | 6.5 ± 1.2 |
| II-OA | 10.9 ± 3.2 | 21.8 ± 2.2 |
| II-OC | 6.9 ± 0.7 | 16.6 ± 4.3 |
| II-OM | 2.0 ± 0.2 | 6.9 ± 2.4 |

[a]Platelets were incubated with ginger extracts or 0.5% DMSO (Control) at 37° C. for 3 min, then arachidonic acid (100 $\mu$M) or collagen (10 $\mu$g/ml) was added to trigger aggregation. Aspirin and Indomethacin are positive controls. The percentage of inhibitory effect is calculated as follows: {[(degree of inhibition of Control) - (degree of inhibition of ginger extract)]/(degree of inhibition of Control)} × 100%
Values are presented as mean ± S.E., n = 3–6.

EXAMPLE 8
Evaluation of Inhibitory Activity on the Carrageenin-induced Paw Edema Inhibitory activity on the carrageenin-induced paw edema was conducted according to the method reported by Winter, C. A. et al. (Winter C. A. et al., Proc. Soc. Exper. Biol. Med. 111: 544–547, 1962.). Male Wistar mice weighing 150±20 g without feeding for one night were injected at left rear paws thereof with 0.1 ml of 1% carrageenin suspension followed by rubbing test samples or vehicle as control on the left rear paws evenly (10 mg/paw). Three hours later, the volumes of the rear paws were determined by using a volume scanner (Cat. #7150, UGO Basil, Italy), and the difference between the left rear paw and the right rear paw was used an index of the carrageenin-induced paw edema.

TABLE 6

Inhibitory activity on the carrageenin-induced paw edema of ginger extracts

| Treatment | Dosage (mg/paw) | Inhibitory activity on the carrageenin-induced paw edema (%) |
|---|---|---|
| I-O | 10 | 18 |
| I-OE | 10 | 19 |
| I-OM | 10 | 29 |
| I-OA | 10 | 25 |
| II-O | 10 | 18 |
| II-OW | 10 | 0 |
| II-OM | 10 | 26 |
| II-OA | 10 | 25 |
| II-OC | 10 | 8 |
| III-O | 10 | 0 |
| III-OM | 10 | 11 |
| III-OA | 10 | 15 |
| [6]-dehydrogingedione | 5 | 26 |

1. Inhibitory activity on the carrageenin-induced paw edema (%) was calculated as follows: [(average degree of edema of mice in the control group) - (average degree of edema of mice in the test group)/(average degree of edema of mice in the control group)] × 100%
2. Values are presented as mean ± S.E., n = 3–6.

What is claimed is:

1. A method of preparing a product potent in anti-inflammation or in anti-platelet aggregation from rhizomes of *Zingiber officinale* comprising the following steps:

a) preparing a crude liquid from rhizomes of *Zingiber officinale*;

b) introducing the crude liquid to a reverse phase chromatography column, and eluting the column with water, a first eluent and a second eluent in sequence, said second eluent having a polarity weaker than that of the first eluent but stronger than that of chloroform, so that a first eluate resulting from elution of the first eluent and a second eluate resulting from elution of the second eluent are obtained;

c) removing the first eluent from the first eluate by evaporation, so that a first concentrated eluate is obtained and is able to be used as the potent product; and d) removing the second eluent from the second eluate by evaporation, so that a second concentrated eluate is obtained and is able to used as the potent product;

wherein step a) comprises steps i) to iv), or comprises step I), step I'), or step I"), wherein said steps i) to iv) are:

i) shedding fresh rhizomes of *Zingiber officinale* and filleting the resulting mixture to obtain a filtrate and a residue;

ii) extracting the filtrate with a first organic solvent, recovering the resulting extraction solution of the first organic solvent, and evaporating the first organic solvent from the extraction solution to obtain a first concentrated extraction solution;

iii) extracting the residue with a second organic solvent, recovering the resulting extraction solution of the second organic solvent, and evaporating the second organic solvent from the extraction solution to obtain a second concentrated extraction solution; and iv) combining the first concentrated extraction solution and the second concentrated extraction solution to obtain the crude liquid;

said step I) is:

I) extracting powder of dried rhizomes of *Zingiber officinale* with the second organic solvent, recovering the resulting extraction solution of the second organic solvent, and evaporating the second organic solvent from the extraction solution to obtain the crude liquid;

said step I') is:

I') steam distilling powder of dried rhizomes of *Zingiber officinale*, and concentrating the resulting distillate by evaporation to obtain the crude liquid; and said step I") is:

I") extracting powder of dried rhizomes of *Zingiber officinale* with supercritical $CO_2$, recovering the resulting extraction solution of the supercritical $CO_2$, and evaporating $CO_2$ from the extraction solution to obtain the crude liquid.

2. The method according to claim 1, wherein the product potent in anti-inflammation or in anti-platelet aggregation comprises 0–10 mg 6-shogaol per gram of the product, 1–150 mg 6-gingerol per gram of the product, and 0–40 mg 6-dehydrogingerdione per gram of the product.

3. The method according to claim 1, wherein said first eluent is methanol, and said second eluent is acetone.

4. The method according to claim 3, wherein step a) comprises steps i) to iv).

5. The method according to claim 4, wherein said first organic solvent is ethyl ether.

6. The method according to claim 4, wherein said second organic solvent is acetone, methanol, ethanol or a combination of them.

7. The method according to claim 6, wherein said second organic solvent is acetone.

8. The method according to claim 3, wherein step a) comprises step I).

9. The method according to claim 8, wherein said second organic solvent is acetone, methanol, ethanol or a combination of them.

10. The method according to claim 9, wherein said second organic solvent is acetone.

11. The method according to claim 3, wherein step a) comprises step I').

12. The method according to claim 3, wherein step a) comprises step I").

13. The method according to claim 3, wherein said reverse phase chromatography column is packed with a porous resin.

14. An anti-inflammation pharmaceutical composition comprising a therapeutically effective amount of a crude liquid prepared in step a) of the method according to claim 1, as an active ingredient, in admixture with a pharmaceutically acceptable carrier or diluent for the active ingredient.

15. The pharmaceutical composition according to claim 14, wherein step a) comprises steps i) to iv).

16. The pharmaceutical composition according to claim 15, wherein said first organic solvent is ethyl ether.

17. The pharmaceutical composition according to claim 16, wherein said second organic solvent is acetone, methanol, ethanol or a combination of them.

18. The pharmaceutical composition according to claim 17, wherein said second organic solvent is acetone.

19. The pharmaceutical composition according to claim 14, wherein step a) comprises step I).

20. The pharmaceutical composition according to claim 19, wherein said second organic solvent is acetone, methanol, ethanol or a combination of them.

21. The pharmaceutical composition according to claim 20, wherein said second organic solvent is acetone.

22. The pharmaceutical composition according to claim 14, wherein step a) comprises step I').

23. The pharmaceutical composition according to claim 14, wherein step a) comprises step I").

24. A pharmaceutical composition for the inhibition of aggregation of platelet, which comprises a therapeutically effective amount of the first concentrated eluate prepared in step c) of the method according to any one of claims 1 to 13, as an active ingredient, in admixture with a pharmaceutically acceptable carrier or diluent for the active ingredient.

25. An anti-inflammation pharmaceutical composition comprising a therapeutically effective amount of the first concentrated eluate prepared in step c) of the method according to any one of claims 1 to 13, as an active ingredient in admixture with a pharmaceutically acceptable carrier or diluent for the active ingredient.

26. An anti-inflammation pharmaceutical composition comprising a therapeutically effective amount of the second concentrated eluate prepared in step d) of the method according to any one of claims 1 to 13, as an active ingredient, in admixture with a pharmaceutically acceptable carrier or diluent for the active ingredient.

27. A pharmaceutical composition for the inhibition of aggregation of platelet, which comprises a therapeutically effective amount of said crude liquid prepared in step a) of the method according to claim 1, as an active ingredient, in admixture with a pharmaceutically acceptable carrier or diluent for the active ingredient.

28. The pharmaceutical composition according to claim 27, wherein step a) comprises steps i) to iv).

29. The pharmaceutical composition according to claim 28, wherein said first organic solvent is ethyl ether.

30. The pharmaceutical composition according to claim 28, wherein said second organic solvent is acetone, methanol, ethanol or a combination of them.

31. The pharmaceutical composition according to claim 30, wherein said second organic solvent is acetone.

32. The pharmaceutical composition according to claim 27, wherein step a) comprises step I).

33. The pharmaceutical composition according to claim 32, wherein said second organic solvent is acetone, methanol, ethanol or a combination of them.

34. The pharmaceutical composition according to claim 33, wherein said second organic solvent is acetone.

35. The pharmaceutical composition according to claim 27, wherein step a) comprises step I').

36. The pharmaceutical composition according to claim 27, wherein step a) comprises step I").

37. A pharmaceutical composition for the inhibition of aggregation of platelet, which comprises a therapeutically effective amount of the second concentrated eluate prepared in step d) of the method according to any one of claims 1 to 13, as an active ingredient, in admixture with a pharmaceutically acceptable carrier or diluent for the active ingredient.

* * * * *

UNITED STATES PATENT AND TRADEMARK OFFICE
CERTIFICATE OF CORRECTION

| | |
|---|---|
| PATENT NO. | : 6,274,177 B1 |
| DATED | : August 14, 2001 |
| INVENTOR(S) | : Tian-Shung Wu, Sheng-Chu Kuo, Che-Ming Teng and Feng-Nien Ko |

It is certified that error appears in the above-identified patent and that said Letters Patent is hereby corrected as shown below:

<u>Title page,</u>
Item [73], the name of the Assignee should read: -- Pharmaceutical Industry Technology and Development Center Taipei Hsien (TW)

Signed and Sealed this

Twenty-fifth Day of June, 2002

*Attest:*

*Attesting Officer*

JAMES E. ROGAN
*Director of the United States Patent and Trademark Office*